(12) United States Patent
Kang et al.

(10) Patent No.: US 10,219,752 B2
(45) Date of Patent: Mar. 5, 2019

(54) APPARATUS AND METHOD FOR ANALYZING LIVING BODY INFORMATION

(71) Applicant: SAMSUNG ELECTRONICS CO., LTD., Suwon-si (KR)

(72) Inventors: Jaemin Kang, Seoul (KR); Yongjoo Kwon, Yongin-si (KR); Sunkwon Kim, Suwon-si (KR)

(73) Assignee: SAMSUNG ELECTRONIC CO., LTD., Suwon-si (KR)

( * ) Notice: Subject to any disclaimer, the term of this patent is extended or adjusted under 35 U.S.C. 154(b) by 361 days.

(21) Appl. No.: 14/992,172

(22) Filed: Jan. 11, 2016

(65) Prior Publication Data

US 2017/0007184 A1    Jan. 12, 2017

(30) Foreign Application Priority Data

Jul. 9, 2015    (KR) ........................ 10-2015-0097863

(51) Int. Cl.
| | | |
|---|---|---|
| *A61B 5/00* | (2006.01) | |
| *A61B 5/02* | (2006.01) | |
| *A61B 5/021* | (2006.01) | |
| *A61B 5/024* | (2006.01) | |
| *A61B 5/026* | (2006.01) | |

(52) U.S. Cl.
CPC ........ *A61B 5/6898* (2013.01); *A61B 5/02007* (2013.01); *A61B 5/02035* (2013.01); *A61B 5/0261* (2013.01); *A61B 5/02125* (2013.01); *A61B 5/7282* (2013.01); *A61B 5/7435* (2013.01); *A61B 5/02141* (2013.01); *A61B 5/02416* (2013.01); *A61B 5/02438* (2013.01);
(Continued)

(58) Field of Classification Search
CPC . A61B 5/6898; A61B 5/02035; A61B 5/0261; A61B 5/7282; A61B 5/7435; A61B 5/02125; A61B 5/02007; A61B 2562/0233; A61B 5/02141; A61B 5/02416; A61B 5/02438; A61B 2560/0462; A61B 2562/04
See application file for complete search history.

(56) References Cited

U.S. PATENT DOCUMENTS

| 7,896,811 B2 | 3/2011 | Han et al. |
| 2002/0169380 A1 | 11/2002 | Hasegawa et al. |
(Continued)

FOREIGN PATENT DOCUMENTS

| EP | 1 618 842 A1 | 1/2006 |
| EP | 1 685 794 A1 | 8/2006 |
| KR | 100340830 B1 | 6/2002 |

OTHER PUBLICATIONS

Communication dated Nov. 9, 2016 issued by the European Patent Office in counterpart European Patent Application No. 16177865.9.
(Continued)

*Primary Examiner* — Tiffany Weston
(74) *Attorney, Agent, or Firm* — Sughrue Mion, PLLC

(57) ABSTRACT

Provided is an apparatus for analyzing living body information including: a plurality of pulse wave sensors configured to detect a pulse wave signal of an object and disposed on a rear surface of the apparatus; a processor configured to analyze living body information of the object based on the detected pulse wave signal; and a display configured to display the analyzed living body information and disposed on a front surface of the apparatus.

21 Claims, 18 Drawing Sheets

(52) U.S. Cl.
CPC ............. *A61B 2560/0462* (2013.01); *A61B 2562/0233* (2013.01); *A61B 2562/04* (2013.01)

(56) References Cited

U.S. PATENT DOCUMENTS

| | | | |
|---|---|---|---|
| 2004/0065098 A1* | 4/2004 | Choi ............. | G05D 23/1931 62/180 |
| 2005/0228297 A1 | 10/2005 | Banet et al. | |
| 2006/0020216 A1* | 1/2006 | Oishi ............. | A61B 5/0205 600/500 |
| 2007/0299322 A1* | 12/2007 | Miyajima ............. | A61B 5/0008 600/301 |
| 2011/0065482 A1* | 3/2011 | Koide ............. | A61B 5/02438 455/566 |
| 2014/0051941 A1* | 2/2014 | Messerschmidt ..... | A61B 5/6898 600/301 |
| 2014/0106816 A1* | 4/2014 | Shimuta ............. | A61B 5/6898 455/556.1 |
| 2014/0114201 A1 | 4/2014 | Watanabe et al. | |
| 2014/0276145 A1 | 9/2014 | Banet et al. | |
| 2017/0007125 A1 | 1/2017 | Kang et al. | |

OTHER PUBLICATIONS

Communication dated Feb. 19, 2018, issued by the European Patent Office in counterpart European Application No. 16177865.9.

* cited by examiner

APPARATUS AND METHOD FOR ANALYZING LIVING BODY INFORMATION

CROSS-REFERENCE TO RELATED APPLICATION

This application claims priority from Korean Patent Application No. 10-2015-0097863, filed on Jul. 9, 2015, in the Korean Intellectual Property Office, the disclosure of which is incorporated herein by reference in its entirety.

BACKGROUND

1. Field

Apparatuses and methods consistent with exemplary embodiments relate to analyzing living body information.

2. Description of the Related Art

As the interest in health increases, various types of apparatuses for detecting living body information are being developed. In particular, while various wearable devices that can be directly worn on a person are supplied, devices specialized in health care are being developed.

A method of detecting living body information, such as a pulse wave, is classified as an invasive method and a noninvasive method. A noninvasive method, whereby a pulse wave is easily detected without causing pain to a person, is frequently used.

To perform accurate pulse wave analysis (PWA), information based on an optical signal or a pressure signal is obtained from a predetermined body surface of a person. Living body information of the person may be obtained based on the information as described above, and various methods are used to reduce measurement errors.

SUMMARY

One or more exemplary embodiments provide apparatuses and methods for analyzing living body information.

According to an aspect of an exemplary embodiment, there is provided an apparatus for analyzing living body information, the apparatus including: a plurality of pulse wave sensors configured to detect a pulse wave signal of an object and disposed on a rear surface of the apparatus; a processor configured to analyze living body information of the object based on the detected pulse wave signal; and a display configured to display the analyzed living body information and disposed on a front surface of the apparatus.

The apparatus may be configured to be held with one hand of a user.

The plurality of pulse wave sensors may include two pulse wave sensors that are positioned to detect pulse wave signals at two points of the hand of the user, the two points being at different distances from the heart of the user when the user holds the apparatus with the hand.

The plurality of pulse wave sensors may include: at least one first pulse wave sensor configured to be positioned to detect a first pulse wave signal from a finger of the user when the user holds the apparatus with one hand; and at least one second pulse wave sensor configured to be positioned to detect a second pulse wave signal from the palm of the hand when the user holds the apparatus with the hand.

The processor may include: a selection unit configured to select two pulse wave sensors among the plurality of pulse wave sensors to obtain a first pulse wave signal and a second pulse wave signal respectively from the selected two pulse wave sensors; and an analyzing unit configured to analyze the living body information based on the first pulse wave signal and the second pulse wave signal.

The object may be a user of the apparatus, and a difference between a first distance, which is measured from one of the two pulse wave sensors to the heart of the user, and a second distance, which is measured from the other pulse wave sensor to the heart, may be equal to or greater than 1 cm when the user holds the apparatus with one hand.

The two pulse wave sensors may be a first pulse wave sensor and a second pulse wave sensor, and the selection unit my be further configured to select the first pulse wave sensor positioned to detect the first pulse wave signal from a finger of the user and the second pulse wave sensor positioned to detect the second pulse wave signal from the palm of the hand when the user holds the apparatus with the hand.

The selection unit may be further configured to select the two pulse wave sensors by comparing signal levels of pulse waves respectively sensed from each of the plurality of pulse wave sensors.

The selection unit may be further configured to receive a user input that instructs the apparatus to select the two pulse wave sensors, and activate the two pulse wave sensors to detect the first pulse wave signal and the second pulse signal.

The analyzing unit may be further configured to extract predetermined characteristic points from the first pulse wave signal and the second pulse wave signal.

The first and second pulse wave signals may be indicated as a function of a voltage variation with respect to time, and the characteristic points may include a peak value of the function.

The analyzing unit may be further configured to calculate a pulse transit time (PTT) from a time difference between a characteristic point of the first pulse wave signal and a corresponding characteristic point of the second pulse wave signal.

The analyzing unit may be further configured to analyze vascular compliance, a blood flow rate, blood viscosity, an arteriosclerosis degree, systolic blood pressure, or diastolic blood pressure based on a distance between the selected two pulse wave sensors and the PTT.

The apparatus may further include a memory configured to store reference values with respect to the living body information of the object.

The processor may include a diagnosis unit configured to compare a result of analyzing the living body information with the reference values, and determine an abnormality of a health state of the object.

The apparatus may further include a wireless communication unit.

The apparatus may be a smartphone.

According to an aspect of another exemplary embodiment, there is provided a method of analyzing living body information, the method including: detecting a first pulse wave signal and a second pulse wave signal respectively from a first point and a second point of a user, the first point and the second point being positioned at a hand of the user and spaced apart from each other; and analyzing living body information based on the first pulse wave signal and the second pulse wave signal.

The one of the two points may be located at a finger of the hand and the other point is located at the palm of the hand.

The two points may be located on one finger of the hand.

The two points may be located at the palm of the hand.

A difference between a first distance, which is measured from one of the two points to the heart of the user, and a second distance, which is measured from the other point to the heart, may be equal to or greater than 1 cm.

The first pulse signal and the second pulse wave signal may be represented as a function of a voltage variation with respect to time. The analyzing may include comparing a peak value of the voltage variation function with a peak value of a differentiation function of the voltage variation function to determine a pulse transit time (PTT), and analyzing the living body information based on the PTT.

The method may further include comparing a result of the analyzing the living body information with a reference value to determine an abnormality of a health state of the user.

According to an aspect of another exemplary embodiment, there is provided a method of analyzing biometric information by a handheld device including a plurality of pulse wave sensors spaced apart from each other, the method including: identifying at least two pulse wave sensors which are in contact with a user among the plurality of pulse wave sensors, the at least two pulse wave sensors comprising a first pulse wave sensor and a second pulse wave sensor; determining a position of the first pulse wave sensor and a position of the pulse wave second sensor; and activating the first pulse wave sensor and the second pulse wave sensor in response to the position of the first pulse wave sensor being included on a list of at least one position that is paired with the position of the second pulse wave sensor or the position of the second pulse wave sensor being included on a list of at least one position that is paired with the position of the first sensor.

The position of the first pulse wave sensor and the position of the second pulse wave sensor are represented by an identifier of the first pulse wave sensor and an identifier of the second pulse wave sensor, respectively.

BRIEF DESCRIPTION OF THE DRAWINGS

The above and/or other aspects will more apparent by describing certain exemplary embodiments, with reference to the accompanying drawings, in which.

DETAILED DESCRIPTION

Figure 1:
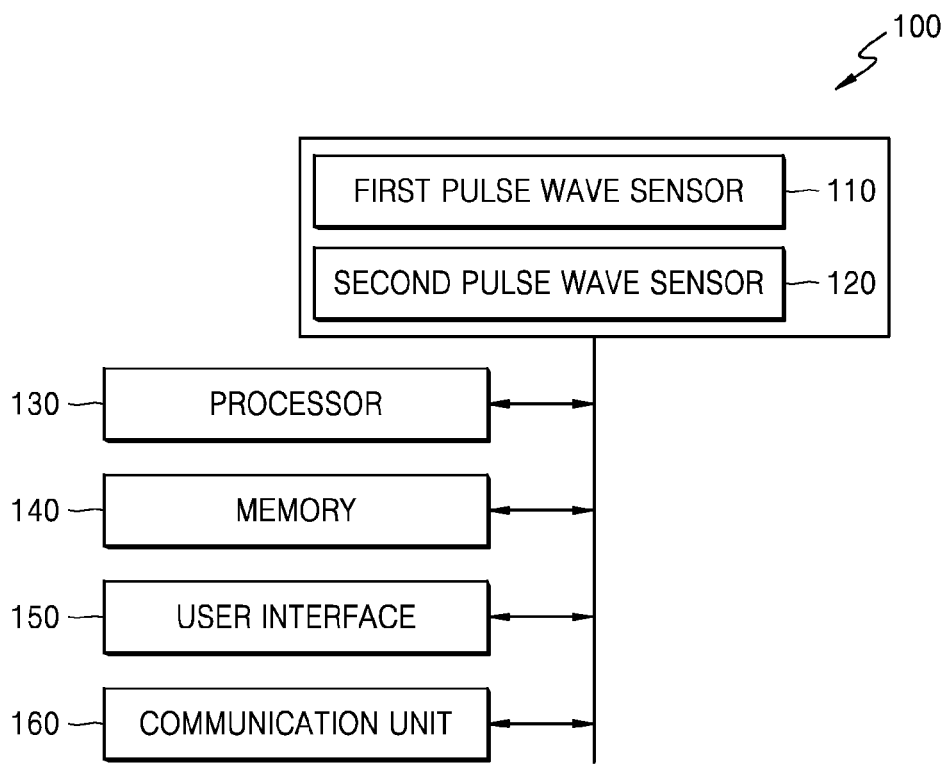
FIG. 1 is a schematic block diagram illustrating an apparatus for analyzing living body information, according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

As used herein, the term "and/or" includes any and all combinations of one or more of the associated listed items. Expressions such as "at least one of," when preceding a list of elements, modify the entire list of elements and do not modify the individual elements of the list.

It will be understood that when a component, such as a layer, a film, a region, or a plate, is referred to as being "on" another component, the component can be directly on the other component or intervening components may be present thereon.

While such terms as "first", "second", etc., may be used to describe various components, such components must not be limited to the above terms. The above terms are used only to distinguish one component from another.

An expression used in the singular encompasses the expression of the plural, unless it has a clearly different meaning in the context. Also, when a part "includes" an element, unless there is a particular description contrary thereto, the part can further include other elements, not excluding the other elements.

In addition, terms such as " . . . unit", " . . . module", or the like refer to units that perform at least one function or operation, and the units may be implemented as hardware or software or as a combination of hardware and software.

Figure 2:
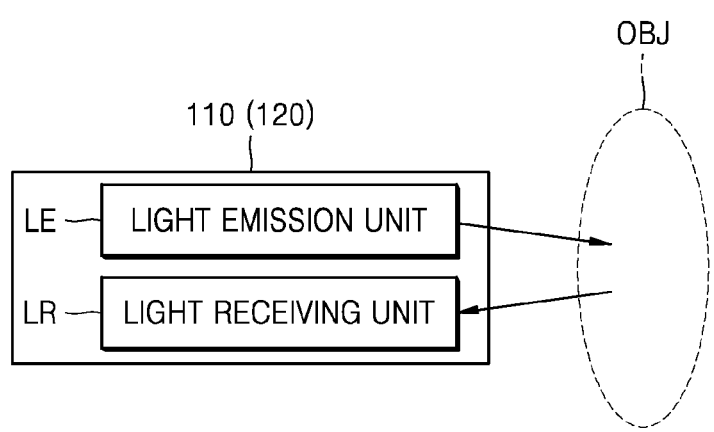
FIG. 2 is a schematic structural block diagram illustrating a pulse wave sensor included in the apparatus for analyzing living body information of FIG. 1.
Figure 3A:
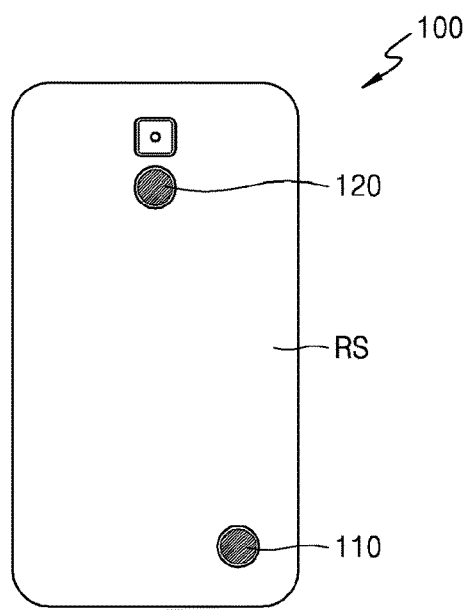
FIGS. 3A and 3B illustrate an apparatus for analyzing living body information according to an exemplary embodiment, wherein a rear surface of the apparatus showing an arrangement of sensors and a front surface of the apparatus being held by a user are respectively shown.
Figure 3B:
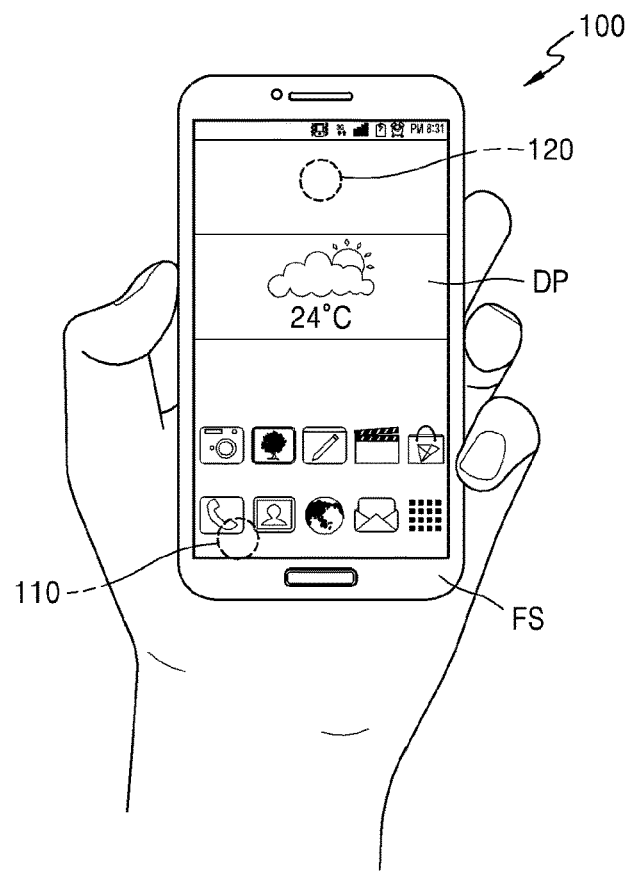

FIG. 1 is a schematic block diagram illustrating an apparatus 100 for analyzing living body information according to an exemplary embodiment. FIG. 2 is a schematic structural block diagram illustrating a pulse wave sensor included in the apparatus 100 for analyzing living body information of FIG. 1. FIGS. 3A and 3B illustrate the apparatus 100 for analyzing living body information according to an exemplary embodiment, wherein a rear surface of the apparatus showing an arrangement of sensors and a front surface of the apparatus being held by a user are respectively shown.

Referring to FIG. 1, the apparatus 100 for analyzing living body information includes first and second pulse wave sensors 110 and 120 detecting a pulse wave signal of an object and a processor 130 analyzing living body information based on a detected pulse wave signal. The apparatus 100 for analyzing living body information may further include a memory 140, a user interface 150, and a communication unit 160.

The apparatus 100 for analyzing living body information according to an exemplary embodiment includes a plurality of pulse wave sensors. The plurality of pulse wave sensors may include the first and second pulse wave sensors 110 and 120 that sense pulse waves at a plurality of points of an on object OBJ. When sensing pulse waves at a plurality of points, a pulse transit time, a pulse wave transfer speed or the like may be additionally acquired, thereby allowing accurate analysis of living body information.

Referring to FIG. 2, the first and second pulse wave sensors 110 and 120 each of which includes a light emission unit (e.g., light emitter) LE emitting light to the object OBJ and a light receiving unit (e.g., light receiver) LR detecting light that is scattered or reflected from the object OBJ. For example, a light emitting diode (LED) or a laser diode may be used as the light emission unit LE. For example, a photo diode, a photo transistor PTr or a charge-coupled device (CCD) may be used as the light receiving unit LR. The light emission unit LE may emit light to the object OBJ, and the light receiving unit LR may detect light that is scattered or reflected from the object OBJ. A pulse wave may be acquired from a detected optical signal.

The object OBJ is an object from which living body information is to be detected and may be a living body portion that may contact or be adjacent to the first and second pulse wave sensors 110 and 120 of the apparatus 100 for analyzing living body information. To detect a pulse wave, the first and second pulse wave sensors 110 and 120 and the object OBJ do not have to completely contact each other, but it is sufficient that the first and second pulse wave sensors 110 and 120 and the object OBJ are adjacent to each other such that a signal-to-noise ratio (SNR) at which a meaningful measurement result may be acquired is realized. Hereinafter, terms such as "contact," "touch," or the like will be described, which should be understood as indicating that elements are adjacent to one another at a degree at which a meaningful result is measured. The meaningful result may refer to a result within a predetermined margin of error.

The object OBJ may be a body portion from which a pulse wave may be easily measured by photoplethysmography (PPG). For example, the object OBJ may be a portion adjacent to a radial artery portion of a wrist surface. When a pulse wave is measured from a skin surface of a wrist through which a radial artery passes, the measurement may be affected relatively little by external factors that cause an error in measurement such as a thickness of a skin tissue inside the wrist. In addition, the radial artery is known as a blood vessel from which a more accurate blood flow than other blood vessel types inside the wrist is measured. The object OBJ may be a body portion of a user who uses the apparatus 100 for analyzing living body information. The object OBJ may be, for example, the hand of the user holding the apparatus 100 for analyzing living body information. Hereinafter, the term "object" may be used interchangeably with the term "user" for convenience of description.

Referring to FIG. 3A, the first and second pulse wave sensors 110 and 120 may be exposed on a rear surface RS of the apparatus 100 as illustrated in FIG. 3A. The first pulse wave sensor 110 may be positioned at a lower end of the rear surface RS, and the second pulse wave sensor 120 may be positioned at an upper end of the rear surface RS. The first and second pulse wave sensors 110 and 120 may be arranged such that, when the user holds the apparatus 100 with the hand, the first and second pulse wave sensors 110 and 120 and a plurality of points of the hand of the user easily contact or abut onto each other spontaneously. As a pulse transit time is to be calculated from pulse wave signals detected from the plurality of points, the first and second pulse wave sensors 110 and 120 may be positioned such that the plurality of points are at two different points that are at different distances from the heart of the object from each other. In addition, if a distance between the first and second pulse wave sensors 110 and 120 is too short, it may be difficult to acquire a meaning result in, for example, a time difference between detected two pulse wave signals. Thus, the distance between the first and second pulse wave sensors 110 and 120 may be at least 1 cm.

Referring to FIG. 3B, the apparatus 100 for analyzing living body information may have a form that can be held by the user with one hand. The apparatus 100 for analyzing living body information may be implemented in the form of a mobile communication device such as a smartphone.

As illustrated in FIG. 3B, when the user holds the apparatus 100 to view a display unit (e.g., display) DP of a front surface FS of the apparatus 100, the first and second pulse wave sensors 110 and 120 of the rear surface RS become touched by the hand of the user. The first pulse wave sensor 110 may contact a palm of the user, and the second pulse wave sensor 120 may contact the fingers of the user. However, this is exemplary, and both the first and second pulse wave sensors 110 and 120 may contact the fingers of the hand or the palm of the user. The user may hold the apparatus 100 in the hand and manipulate the same while viewing a screen shown on the display unit DP, and may also view an analysis result.

As the first and second pulse wave sensors 110 and 120 are positioned on the rear surface RS of the apparatus 100 as described above, the user may easily contact the first and second pulse wave sensors 110 and 120. For example, even during normal usage where measurement is not intended, the pulse wave sensors may be in contact with the body of the user. Thus, the apparatus 100 may be used to analyze and store living body information of the user in an automatic mode, thereby increasing user convenience.

Figure 4:
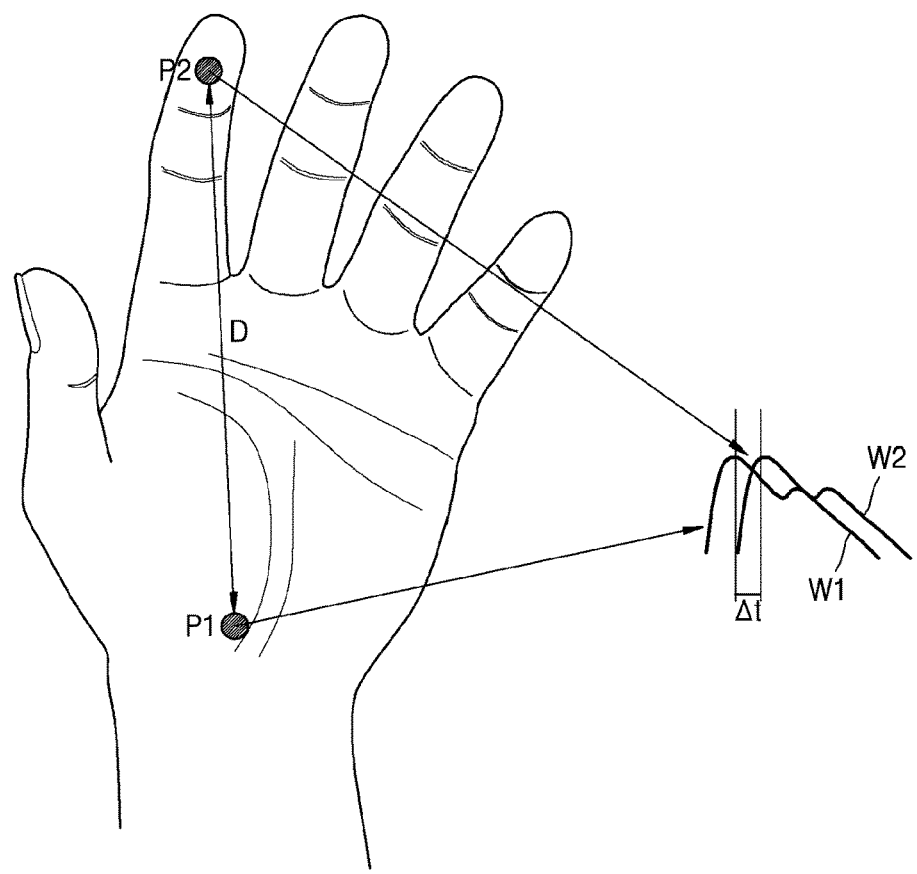
FIG. 4 is a conceptual diagram illustrating a method of measuring a pulse wave, performed by using an apparatus for analyzing living body information, according to an exemplary embodiment.

FIG. 4 is a conceptual diagram illustrating a method of measuring a pulse wave, performed by using the apparatus 100 for analyzing living body information, according to an exemplary embodiment.

Pulse waves are detected from two points of an object OBJ of the apparatus 100. That is, a pulse wave signal that is close to the heart and a pulse wave signal close to an end of the body are detected. P1 and P2 denote two points of the object OBJ from which pulse waves are to be detected. The point P1 is closer to the heart than the point P2. W1 denotes a pulse wave signal detected from the point P1, and W2 denotes a pulse wave signal detected from the point P2. An interval Δt between respective peak points of the two pulse wave signals W1 and W2 may denote a pulse transit time (PPT). In order to acquire the interval Δt, time differential functions of the two pulse waves W1 and W2 may be used. A pulse transit speed may be calculated from a distance D between the two points P1 and P2 from which the respective pulse waves W1 and W2 are measured and the interval Δt.

A transit speed of a pulse wave traveling along an artery may be about 1 m/s to about 5 m/s, and the smaller a distance between two points from which signals are measured, the shorter is a signal transit time between the two points. Thus, the smaller a distance between the two points from which pulse wave signals are sensed, the higher a sampling frequency may be required for signal measurement. That is, an amount of data to be processed is increased and thus a calculation amount of the entire system is increased, and power consumption is also increased. To solve this, additional circuit elements such as a differentiator, an integrator, a comparator, a peak detector or the like are to be added, and implementation of a system is difficult. According to the apparatus 100 for analyzing living body information of the exemplary embodiment, a sufficient distance between the two points is provided so that living body information may be analyzed without an increase in a calculation amount or without introducing a complicated system.

Figure 5A:
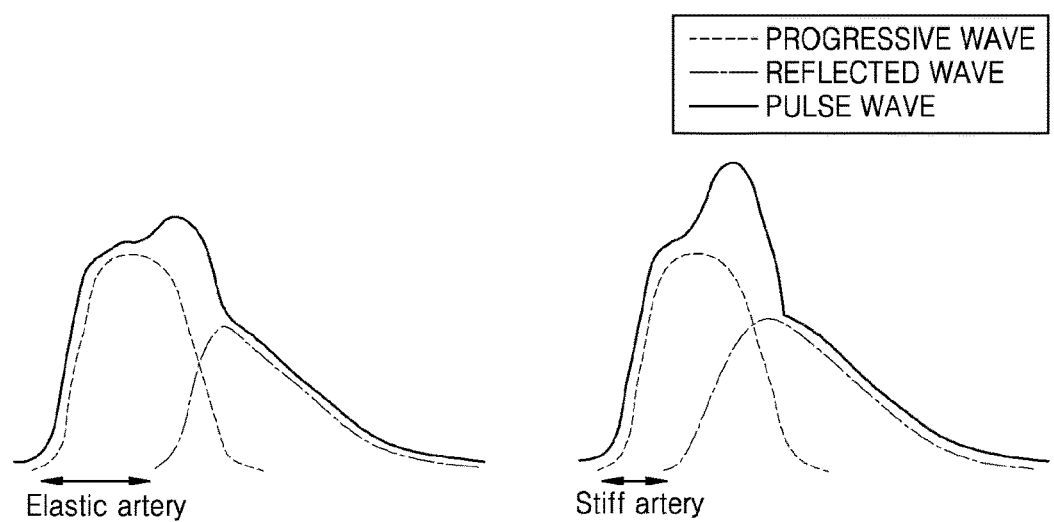
FIGS. 5A through 5C illustrate a pulse wave measured using a pulse wave sensor of an apparatus for analyzing living body information, according to an exemplary embodiment.
Figure 5B:
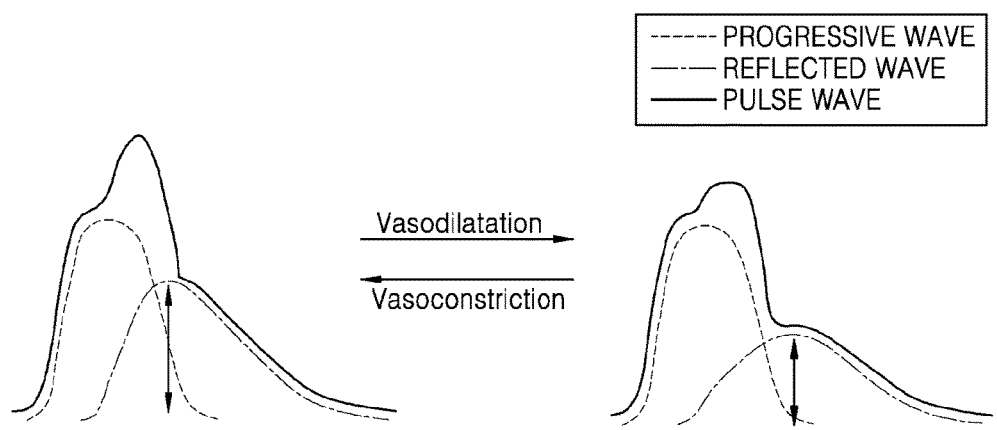
Figure 5C:
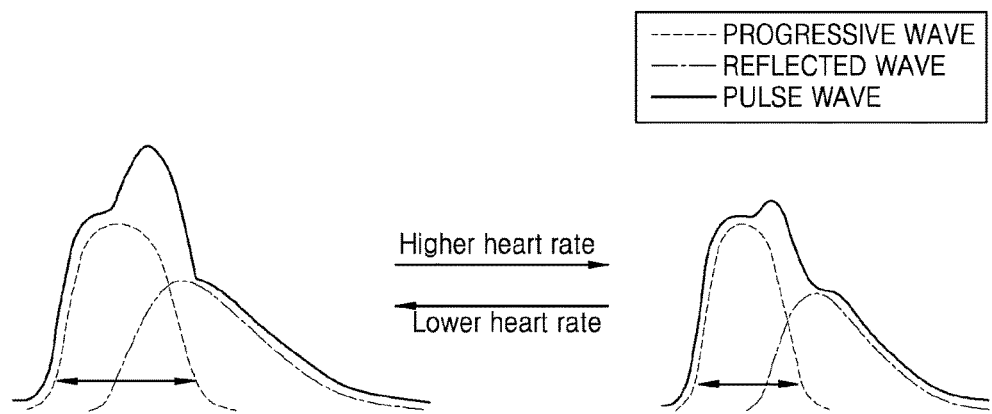
Figure 6:
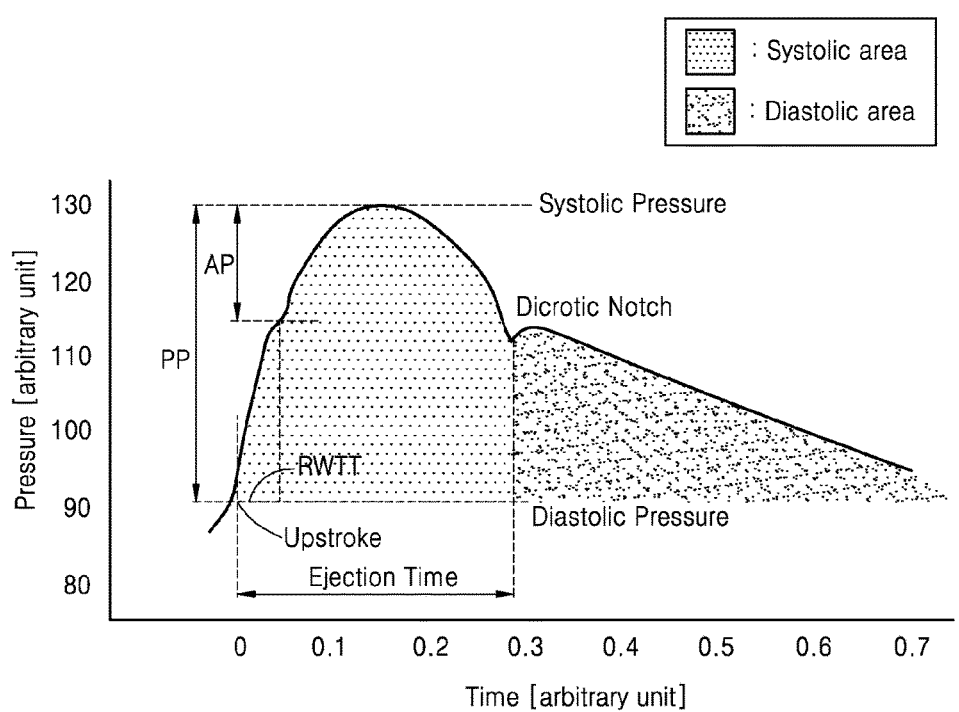
FIG. 6 illustrates living body information that is extracted from a waveform of a pulse wave.
Figure 7:
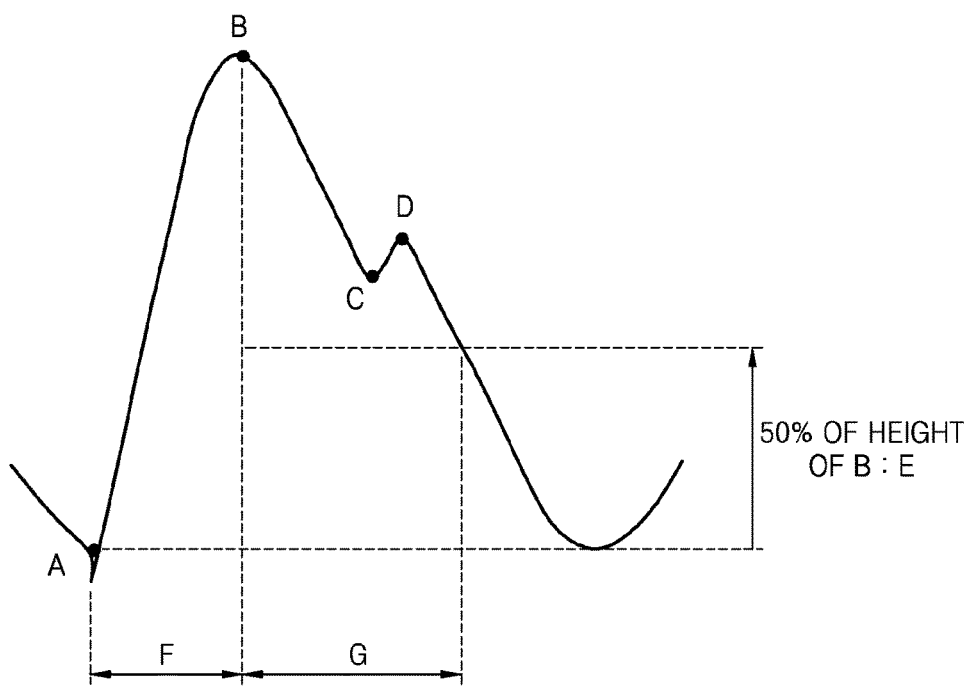
FIG. 7 illustrates pulse wave characteristic points extracted by using a pulse wave characteristic point extracting unit.

FIGS. 5A through 5C illustrate a pulse wave measured using a pulse wave sensor of the apparatus 100 according to an exemplary embodiment. FIG. 6 illustrates living body information that is extracted from a waveform of a pulse wave. FIG. 7 illustrates pulse wave characteristic points.

As illustrated in FIGS. 5A through 5C, a pulse wave includes a progressive wave that proceeds outward from the heart after being generated therein and a reflected wave that returns from a distal portion, and the progressive wave and the reflected wave overlap each other to form the pulse wave. A form of a pulse wave reflects a cardiovascular condition or a blood pressure or the like, and thus various types of information may be obtained from pulse wave analysis (PWA).

For example, FIG. 5A shows that a reflected wave propagates faster when a vascular stiffness is higher, and the vascular stiffness may be determined to indicate either an elastic artery or a stiff artery based on a propagation time of the reflected wave. In addition, FIG. 5B shows that amplitude of a reflected wave relates to expansion and contraction of blood vessels, and FIG. 5C shows a factor related to a heart rate. As shown in FIG. 5B, the amplitude of the reflected wave while blood vessels are contracted may be greater than the amplitude of the reflected wave while the blood vessels are widen. In greater detail, FIG. 5C illustrates that the time period which is taken for the progressive wave to complete one cycle may decrease as the heart rate increases.

FIG. 6 shows living body information that may be extracted from a waveform of a pulse wave that is exhibited by overlapping or augmentation of a progressive wave and a reflected wave. For example, a pulse pressure (PP) is shown by a difference between a systolic pressure and a diastolic pressure. A mean blood pressure is shown by a diastolic pressure+PP/3, and may reflect a load on the heart. In addition, a value exhibiting an augmentation pressure (AA) out of the PP (AP/PP) may be represented as a percentage (%) and may indicate an augmentation index (AI). The value of AA/PP may reflect vascular compliance and load on a left ventricle. A reflective wave transit time (RWTT) may reflect a vascular stiffness. A subendocardinal viability index (SERV) exhibited by diastolic area/systolic area may reflect a state of a coronary artery such as a state of coronary artery flow or a possibility of coronary artery disease. In addition, an ejection time, which is a time interval from a systolic upstroke to a dicrotic notch, may be measured to determine a state of a heart muscle contraction force. These indices relate to hypertension (division of borderline hypertension), cardiac insufficiency (division of systolic dysfunction and diastolic dysfunction), early diagnosis of cardiovascular complication in diabetes, determination of ischemic heart disease, or the like, and may be used clinically for prescription of medication or optimized treatment, and are acquired using only an invasive method in the related art.

By considering the indices as described above, characteristic points A, B, C, and D shown in FIG. 7 may be extracted from a waveform of a pulse wave and feature values E, F, and G may be calculated from the characteristic points A and B. Feature points A, B, C, and D may correspond to a systolic upstroke, a peak systolic pressure, a dicrotic notch, and a peak dicrotic pressure, respectively. For example, an extreme value of a differential signal of a pulse wave may be added as a characteristic point. A differential signal of a pulse wave is sharper than a pulse wave signal and thus an error thereof caused by noise may be relatively small.

Figure 8:
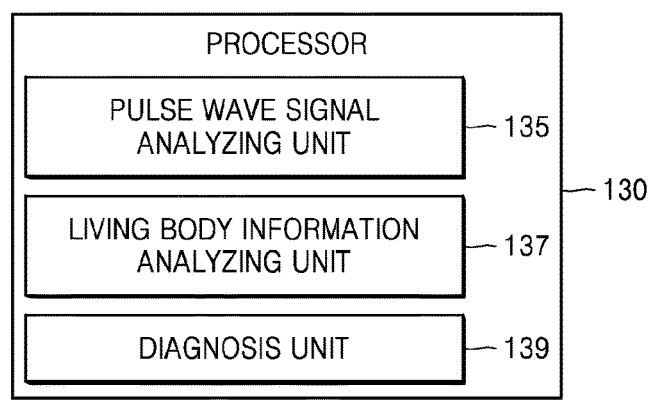
FIG. 8 is a schematic structural block diagram illustrating a processor illustrated in FIG. 1.

FIG. 8 is a schematic structural block diagram illustrating a processor 130 illustrated in FIG. 1.

The processor 130 may include a pulse wave signal analyzing unit 135 analyzing a pulse wave signal detected from the first and second pulse wave sensors 110 and 120 and a living body information analyzing unit 137 analyzing living body information based on a result of analyzing the pulse wave signal. Also, the processor 130 may further include a diagnosis unit 139 determining a health state of an object based on the analyzed living body information.

The pulse wave signal analyzing unit 135 may extract pulse wave characteristic points as shown in FIG. 7 from two pulse wave signals. Also, the pulse wave signal analyzing unit 135 may calculate a pulse transit time, a pulse transit speed or the like from a time difference between two pulse waves or a distance between two pulse wave sensors. To this end, the pulse wave signal analyzing unit 135 may include an analog signal processor, an analog to digital converter (ADC), a digital signal processor, or the like, and may use various signal processing algorithms such as a noise removing algorithm or a differential signal extraction algorithm.

The living body information analyzing unit 137 may detect various types of living body information by using the result obtained using the pulse wave signal analyzing unit 135. The living body information analyzing unit 137 may estimate, for example, vascular compliance, a blood flow rate, a blood viscosity, an arteriosclerosis degree, a systolic blood pressure or a diastolic blood pressure. Various estimation formulae or look up tables or the like that calculate predetermined living body information from the above-described characteristic points may be used to analyze living body information based on a result of analyzing a pulse wave signal.

The diagnosis unit 139 may determine an abnormality of a health state of an object based on the analyzed living body information. For example, analyzed values may be compared with a reference value with respect to living body information that corresponds to the analyzed values and is stored in the memory 140 of the apparatus 100. The reference value may be normal range value that is previously input with respect to the corresponding living body information or may be an average of results measured during a predetermined period by using the apparatus 100.

Other elements of the apparatus 100 will be described by referring to FIG. 1 again.

Programs for processing and controlling the processor 130 and input or output data may be stored in the memory 140. For example, programs for analysis of pulse waves, analysis of living body information, and diagnosis described above, which are respectively performed by the pulse wave signal analyzing unit 135, the living body information analyzing unit 137, and the diagnosis unit 139 in the processor 130 may be stored as codes. In addition, detection results of the first and second pulse wave sensors 110 and 120 may be stored in the memory 140 so that the processor 130 performs operations based on the stored results. Body information of the user such as the age, gender, height or weight, the date and time when a living body signal is detected, and analyzed living body information or the like may be stored in the memory 140. Also, reference information needed for diagnosis performed by the diagnosis unit 139 may be stored in the memory 140. For example, an average range of living body information of an object calculated from living body information that is measured and stored may be stored in the memory 140. In addition, a normal range of living body information that is obtained by considering the body information of the user may be stored in the memory 140.

The memory 140 may include at least one type of storage medium selected from a flash memory type, a hard disk type, a multimedia card micro type, a card type memory (e.g., a SD or XD memory), a random access memory (RAM), a static RAM (SRAM), a read-only memory (ROM), an electrically erasable programmable ROM (EEPROM), a programmable ROM (PROM), a magnetic memory, a magnetic disk, and an optical disk.

The user interface 150 is an interface between the apparatus 100 for analyzing living body information and a user and/or other external devices, and includes an input unit and an output unit. The user may be an object from which living body information is to be measured, that is, an object OBJ, but may also be a person who is able to use the apparatus 100, such as a medical specialist, and may be a broader concept than the object OBJ. Information needed to operate the apparatus 100 may be input via the user interface 150, and an analysis result may be output. The user interface 150 may include, for example, a button, a connector, a keypad, a display, or a touch display, and may further include a sound output unit or a vibration motor or the like.

The communication unit 160 may communicate with other devices. For example, an analysis result may be transmitted to other external devices via the communication unit 160. An external device may be medical equipment that uses the analyzed living body information, a printer printing a result, or a display device displaying an analysis result. In addition, the communication unit 160 may be, without limitation, a smartphone, a portable phone, a personal digital assistant (PDA), a laptop, a personal computer (PC), or other mobile or non-mobile computing devices.

The communication unit 160 may communicate with an external device via, without limitation, a Bluetooth communication method, a Bluetooth Low Energy (BLE) communication method, a Near field communication (NFC) method, a wireless local area network (WLAN) communication method, a Zigbee communication method, an infrared Data Association (IrDA) communication method, a Wi-Fi Direct (WFD) communication method, a Ultra Wideband (UWB) communication method, an Ant+ communication method, a Wi-Fi communication method or the like.

Figure 9:
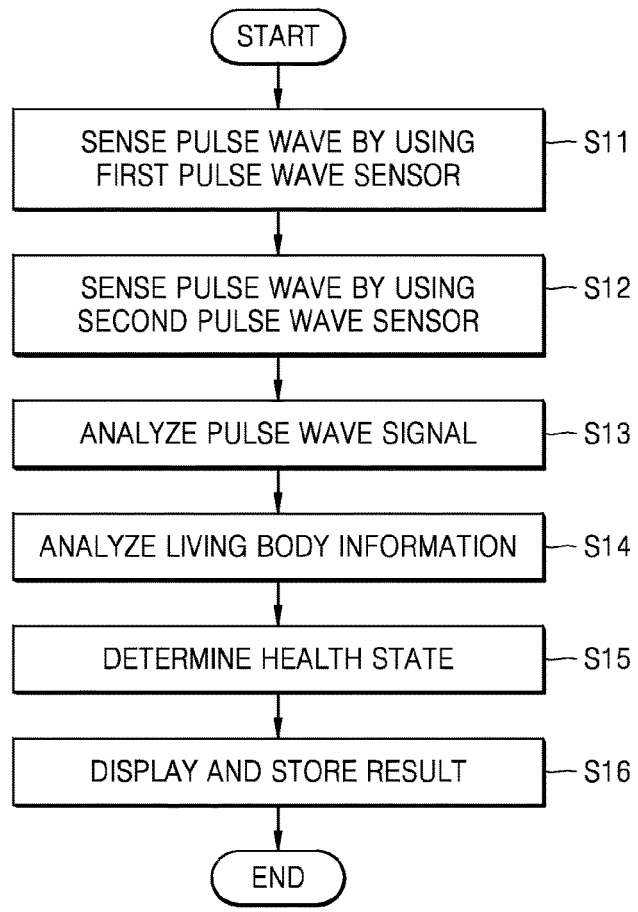
FIG. 9 is a flowchart of a method of analyzing living body information according to an exemplary embodiment.

FIG. 9 is a flowchart of a method of analyzing living body information according to an exemplary embodiment.

The method of analyzing living body information according to an exemplary embodiment may be performed using the apparatus 100 for analyzing living body information. For example, as illustrated in FIG. 3B, analysis of living body information may be performed while the user is holding the apparatus 100 in the hand. The first pulse wave sensor 110 may contact or be adjacent to the palm of the user, and the second pulse wave sensor 120 may contact or be adjacent to the fingers of the user. The first pulse wave sensor 110 and the second pulse wave sensor 120 respectively detect a pulse wave from the palm and the fingers in operations S11 and S12.

Next, detected pulse wave signals are analyzed in operation S13. Various characteristic points, indices related to living body information or the like may be calculated from the detected pulse wave signals. For example, a pulse transit time or a pulse transit speed may be calculated.

Next, various types of living body information is analyzed by using a result of analyzing the pulse wave signals in operation S14. For example, vascular compliance, a blood flow rate, a blood viscosity, an arteriosclerosis degree, a systolic blood pressure or a diastolic blood pressure may be estimated. To analyze living body information, various estimation formulae or lookup tables or the like that calculate predetermined living body information from various factors extracted from pulse wave signals may be used.

A health state of a user, that is, of an object, may be determined based on the analyzed living body information in operation S15. For example, whether the living body information is within a normal range may be determined and an abnormality of the health state of the object may be determined. To determine details as above, reference values stored in a memory may be used. The reference values may be normal range values that are previously input with respect to corresponding living body information, or may be an average of results that are measured during a predetermined period by using the apparatus 100.

The analyzed results may be displayed on a display unit, and may also be stored in the memory in operation S16. A result stored in the memory may also be used to update previously stored reference values.

Operations S11 through S16 may be repeated in predetermined periods. For example, if the apparatus 100 is implemented in the form of a portable communication device, a user may carry the apparatus 100 in daily life. Thus, living body information as described above may be analyzed once a week or once a month, or every day or several times a day, depending on a health state of the user, and a result of analyzing the living body information may be stored in the apparatus 100 and used to monitor health of the user.

Figure 10:
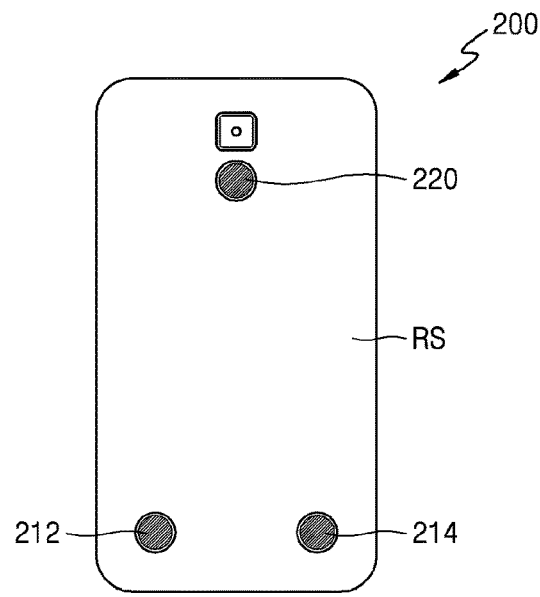
FIG. 10 illustrates an apparatus for analyzing living body information according to another exemplary embodiment.

FIG. 10 illustrates an apparatus 200 for analyzing living body information 200 according to another exemplary embodiment.

The apparatus 200 for analyzing living body information includes a 1-1 pulse wave sensor 212 and a 1-2 pulse wave sensor 214 positioned at a lower end of a rear surface thereof, and a second pulse wave sensor 220 positioned at an upper end of the rear surface thereof.

Arrangement of the pulse wave sensors is to allow a user to easily contact the pulse wave sensors. That is, the pulse wave sensors may spontaneously contact the body of the user even during normal usage when measurement is not intended. In particular, when the user holds the apparatus 200 for analyzing living body information with the left hand or the right hand, one of the 1-1 pulse wave sensor 212 and the 1-2 pulse wave sensor 214 that are positioned at the lower end may touch the palm of the user.

Figure 11A:
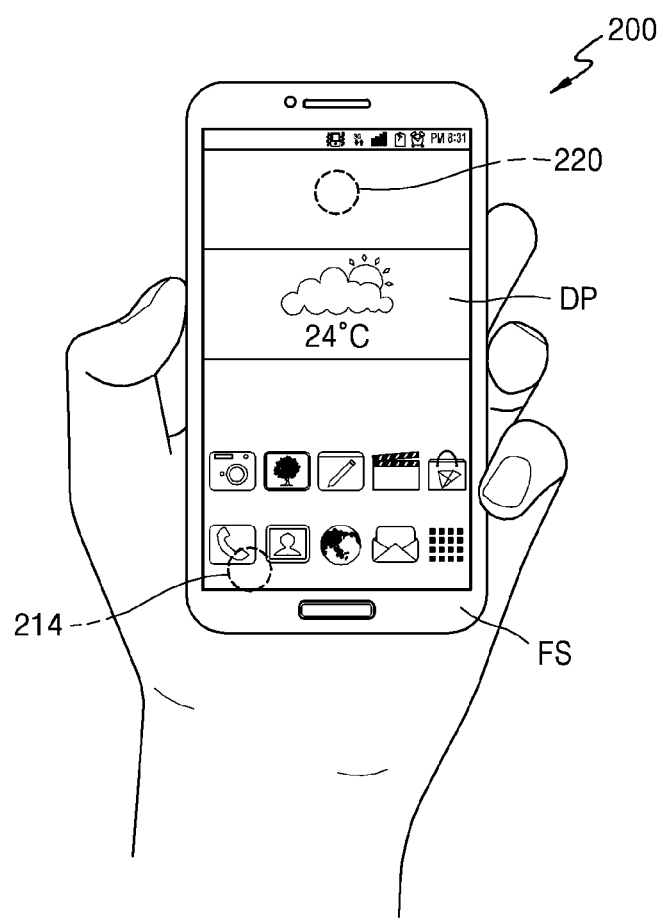
FIGS. 11A and 11B respectively illustrate examples in which a user holds the apparatus for analyzing living body information of FIG. 10 with the left hand and with the right hand, wherein pulse wave sensors located at different positions are touched in the respective examples.
Figure 11B:
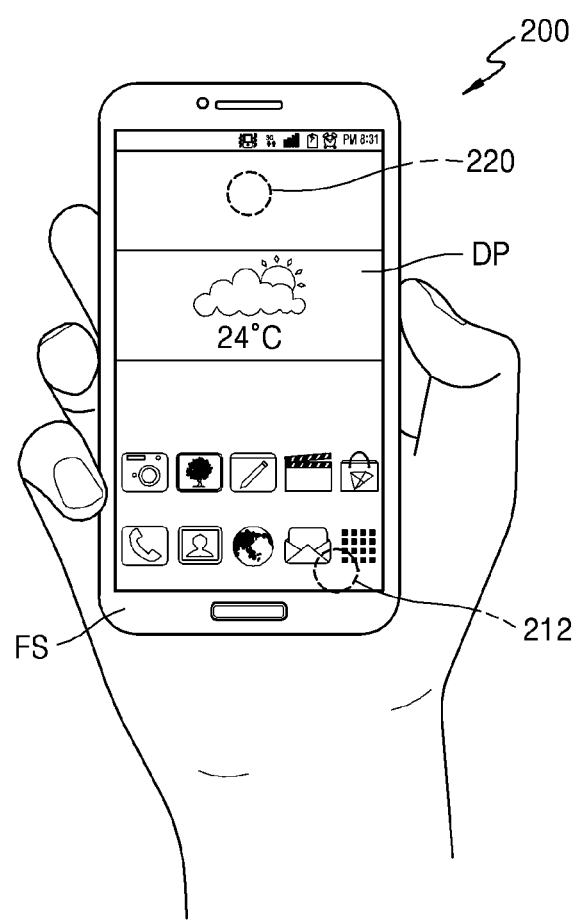

FIGS. 11A and 11B respectively illustrate examples in which a user holds the apparatus 200 for analyzing living body information of FIG. 10 with the left hand and with the right hand, wherein pulse wave sensors located at different positions are touched in the respective examples.

Referring to FIG. 11A, when the user holds the apparatus 100 with the left hand so as to view a front surface FS having a display unit DP, the 1-2 pulse wave sensor 214 and the second pulse wave sensor 220 on the rear surface respectively contact or are adjacent to the palm and the fingers of the user.

Referring to FIG. 11B, when the user holds the apparatus 200 with the right hand so as to view the front surface FS having the display unit DP, the 1-1 pulse wave sensor 212 and the second pulse wave sensor 220 on the rear surface respectively contact or are adjacent to the palm and the fingers of the user.

In the above exemplary embodiment, two or three pulse wave sensors are described. However, more pulse wave sensors may be included to enhance user convenience.

Figure 12:
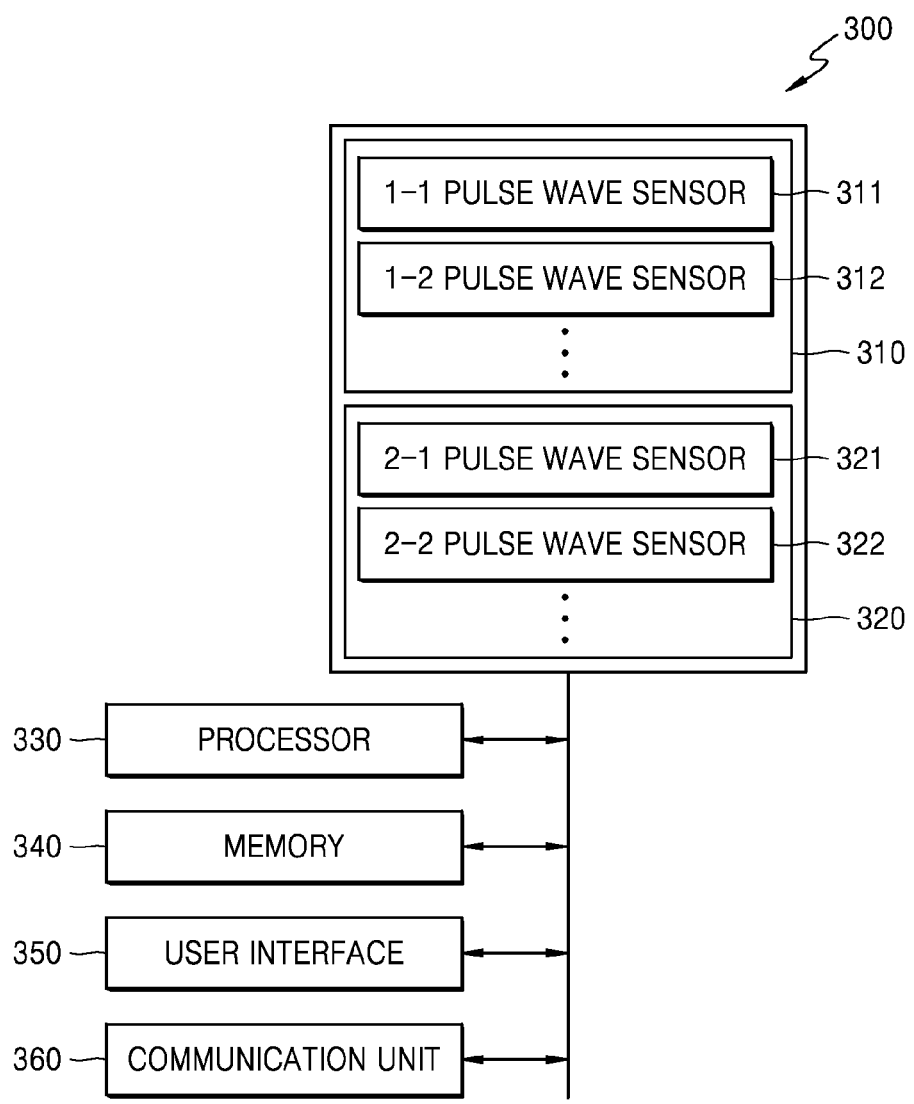
FIG. 12 is a schematic block diagram illustrating an apparatus for analyzing living body information, according to another exemplary embodiment.
Figure 13:
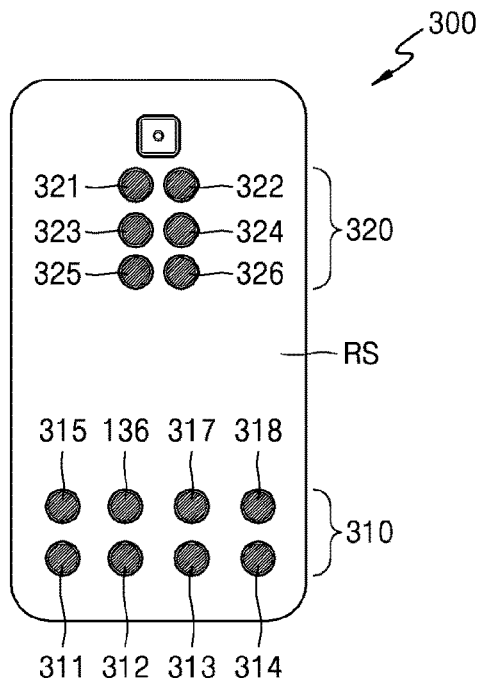
FIG. 13 illustrates the apparatus for analyzing living body information of FIG. 12, in which an exemplary arrangement of a plurality of pulse wave sensors is illustrated.
Figure 14:
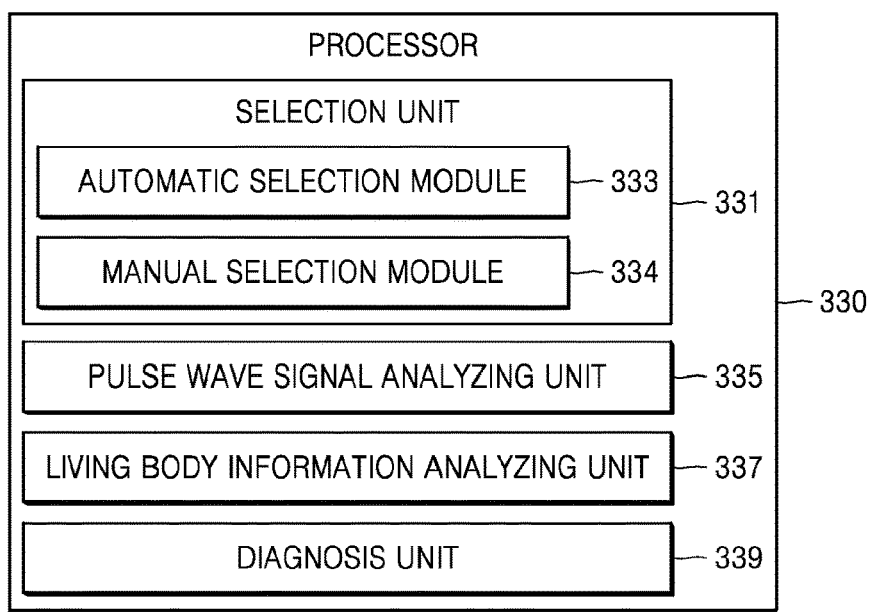
FIG. 14 is a schematic block diagram illustrating a processor illustrated in FIG. 12.

FIG. 12 is a schematic block diagram illustrating an apparatus 300 for analyzing living body information according to another exemplary embodiment. FIG. 13 illustrates the apparatus 300 for analyzing living body information of FIG. 12, where an arrangement of a plurality of pulse wave sensors is illustrated. FIG. 14 is a schematic block diagram illustrating a processor 330 illustrated in FIG. 12.

Referring to FIGS. 12 and 13, the apparatus 300 includes a first pulse wave sensor group 310 and a second pulse wave sensor group 320. The apparatus 300 may include the processor 330 that analyzes a pulse wave signal and living body information, and may further include a memory 340, a user interface 350, and a communication unit 360.

The first pulse wave sensor group 310 includes a 1-1 pulse wave sensor 311, a 1-2 pulse wave sensor 312, a 1-3 pulse wave sensor 313, a 1-4 pulse wave sensor 314, a 1-5 pulse wave sensor 315, a 1-6 pulse wave sensor 316, a 1-7 pulse wave sensor 317, and a 1-8 pulse wave sensor 318 that are positioned at a lower portion of a rear surface of the apparatus 300. The second pulse wave sensor group 320 includes a 2-1 pulse wave sensor 321, a 2-2 pulse wave sensor 322, a 2-3 pulse wave sensor 323, a 2-4 pulse wave sensor 324, a 2-5 pulse wave sensor 325, and a 2-6 pulse wave sensor 326 that are positioned at an upper portion of a rear surface RS of the apparatus 300 for analyzing living body information. The number of the pulse wave sensors is exemplary, and may also be modified.

Arrangement of the pulse wave sensors as described above allows at least two of the pulse wave sensors to easily contact an object regardless of various body conditions of the user who is using the apparatus 300, for example, regardless of a size of the hand, whether the user is a left-hander, or the habit of the user holding the apparatus 300 such as a form of holding the apparatus 300 in the hand.

Referring to FIG. 14, in order to detect pulse wave signals from at least two of the plurality of pulse wave sensors, the processor 330 includes a selection unit 331 that selects two of the pulse wave sensors so that pulse wave signals respectively detected from the selected two pulse wave sensors are used in analysis of living body information. The processor 330 also includes a pulse wave signal analyzing unit 335, a living body information analyzing unit 337, and a diagnosis unit 339.

For example, the selection unit 331 may select one pulse wave sensor from the first pulse wave sensor group 310 and one pulse wave sensor from the second pulse wave sensor group 320. When the object holds the apparatus 300 with one hand, the selection unit 331 may select, from among the plurality of pulse wave sensors, one pulse wave sensor that is positioned such that a pulse wave signal is detected from the finger of the object and one pulse wave sensor that is positioned such that a pulse wave signal is detected from the palm of the object. However, this is exemplary, and the exemplary embodiments are not limited thereto.

The selection unit 331 may select and activate two pulse wave sensors from the first pulse wave sensor group 310 or two pulse wave sensors from the second pulse wave sensor group 320 when a predetermined requirement is met. The predetermined requirement may be, for example, a distance between the two pulse wave sensors. If a distance between selected two pulse wave sensors is too short, it may be difficult to detect a meaningful time difference between pulse wave signals detected from the two pulse wave sensors. A distance between the selected two pulse wave sensors may be 1 cm or more. In addition, while the user is holding the apparatus 300 in the hand, a difference in respective distances between the heart of the user and the respective two pulse wave sensors may be 1 cm or more. That is, the selected two pulse wave sensors are to be located to contact two points of the body that are on a path, through which a pulse wave transits from the heart to an end of the body. For example, selection of two pulse wave sensors is not suitable when, although a distance between the two pulse wave sensors is 1 cm or more, respective distances from the heart to the two pulse wave sensors are the same or a difference between the respective distances is less than 1 cm. When the selection unit 331 selects pulse wave sensors, a contact state between the pulse wave sensors and the object is also to be considered.

According to another exemplary embodiment, the selection unit 331 may identify at least two sensors, among the plurality of sensors 311-318 and 321-326, which are in contact with the hand of the user. For example, with reference to FIG. 13, the identified sensors may be the 2-1 pulse wave sensor 321 and the 2-6 pulse wave sensor 326. The processor 330 may determine the position of the 2-1 pulse wave sensor 321 and the position of the 2-6 pulse wave sensor 326. The processor 330 may activate the 2-1 pulse wave sensor 321 and the 2-6 pulse wave sensor 326 based on a list of paired sensors which is stored in the memory 140. For example, the list of paired sensor may include a first list of positions which are paired with the position of the 2-1 pulse wave sensor 321 and a second list of positions which are paired with the position of the 2-6 pulse wave sensor 326. The first list may include positions of sensors which are spaced apart from the 2-1 pulse wave sensor 321 by a predetermined distance (e.g., 1 cm) in the longitudinal axis direction of the apparatus 300. For example, the first list may include the positions of the 2-5 pulse wave sensor 325, a 2-6 pulse wave sensor 326, and all the sensors included in the first pulse wave sensor group 310. The second list may include the positions of the 2-1 pulse wave sensor 321, the 2-2 pulse wave sensor 322, and all the sensors included in the first pulse wave sensor group 310. If the processor 330 determines that the position of the 2-1 pulse wave sensor 321 is included on the second list, or the position of the 2-6 pulse wave sensor 326 is included on the first list, the processor 330 activates the 2-1 pulse wave sensor 321 and the 2-6 pulse wave sensor 326. The list of paired sensors may include identifiers of the plurality of sensors 311-318 and 321-326 that are associated with the positions of the plurality of sensors 311-318 and 321-326, in addition or alternatively to the position information.

To select pulse wave sensors according to the above conditions, the selection unit 331 may include an automatic selection module 333 and a manual selection module 334.

The automatic selection module 333 senses pulse waves from a plurality of pulse wave sensors and compares signal levels of sensed pulse waves so as to select two pulse wave sensors. SNRs of detected pulse wave signals may differ according to contact states between the pulse wave sensors and the object. Also when the contact states are similar, SNRs of the detected pulse wave signals may differ according to how much the pulse wave sensors are adjacent to a radial artery. Two optimum pulse wave sensors may be selected by respectively sensing pulse waves from a plurality of pulse wave sensors and considering SNRs of the detected pulse wave signals. In this case, also, it may be considered that a predetermined distance between the two pulse wave sensors is ensured, that is, that a predetermined difference between distances from the two pulse wave sensors and the heart of the object is ensured. A difference in distances between the heart and the two pulse wave sensors may be slightly different according to a way in which the user holds the apparatus 300 in the hand. Thus, in order to secure a distance between selected two pulse wave sensors, the selection unit 331 may select one pulse wave sensor from the first pulse wave sensor group 310 and one pulse wave sensor from the second pulse wave sensor group 320. In other words, a pulse wave sensor having a relatively great SNR may be selected from the first pulse wave sensor group 310, and a pulse wave sensor having a relatively great SNR may be selected from the second pulse wave sensor group 320.

The manual selection module 334 receives a user input regarding selection of pulse wave sensors and senses a pulse wave from selected pulse wave sensors.

A posture of holding the apparatus 300 in the hand may vary depending on users, and also depending on body conditions of users. While a user is holding the apparatus 300 in the hand, the user may select two pulse wave sensors determined as being suitable. The apparatus 300 for analyzing living body information may detect pulse wave signals by operating two pulse wave sensors that are determined according to a user input, and analyze living body information base on the detected pulse wave signal.

Figure 15:
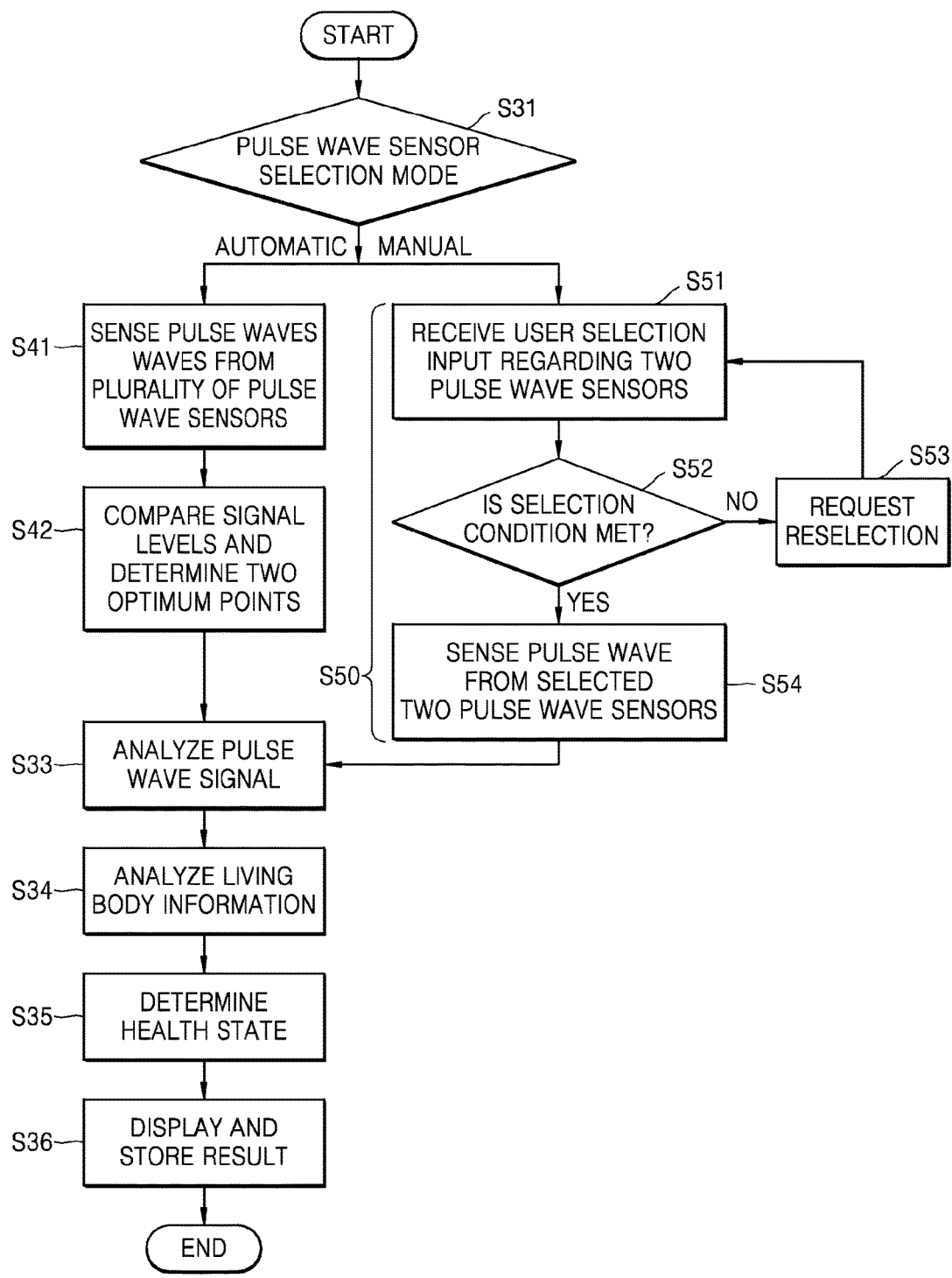
FIG. 15 is a flowchart of a method of analyzing living body information, according to another exemplary embodiment.

FIG. 15 is a flowchart of a method of analyzing living body information according to another exemplary embodiment. FIGS. 16A through 16F illustrate screens on which a manual selection mode of the apparatus 300 for analyzing living body information of FIG. 12 is performed according to the flowchart of FIG. 15.

The method of analyzing living body information may be performed using the apparatus 300 with reference to FIGS. 12 through 14. Description below will focus on an exemplary embodiment in which the method is performed using the apparatus 300.

In a pulse wave sensor selection mode in operation S31, an automatic mode or a manual mode may be selected.

When an automatic mode is selected, the apparatus 300 senses pulse waves from a plurality of pulse wave sensors in operation S41.

Next, signal levels of sensed pulse waves are compared to determine pulse wave sensors that are at two optimum points in operation S42. Here, SNRs of the sensed pulse wave signals may be compared with one another. In addition, two pulse wave sensors may be selected by considering a predetermined sufficient distance between the selected two pulse wave sensors.

When a manual mode is selected, the apparatus 300 first receives a user input regarding selection of two pulse wave sensors in operation S51.

Next, whether a selection condition is met or not is determined in operation S52. For example, whether a distance between the selected two pulse wave sensors, that is, a difference in distances from the heart to the two pulse wave sensors is equal to or greater than a predetermined value, and whether the two pulse wave sensors are located to contact two points that are on a path of a pulse wave traveling from the heart of the object to a body end of the object are determined. Also, it is determined whether the selected two pulse wave sensors properly contact the object. In determination of the above, the selected two pulse wave sensors may be operated to determine whether an SNR of a detected pulse wave signal is equal to or greater than a predetermined value.

If it is determined that the above conditions are met, a pulse wave is sensed from selected two pulse wave sensors in operation S54, and if the conditions are not met, reselection is requested in operation S53.

Figure 16A:
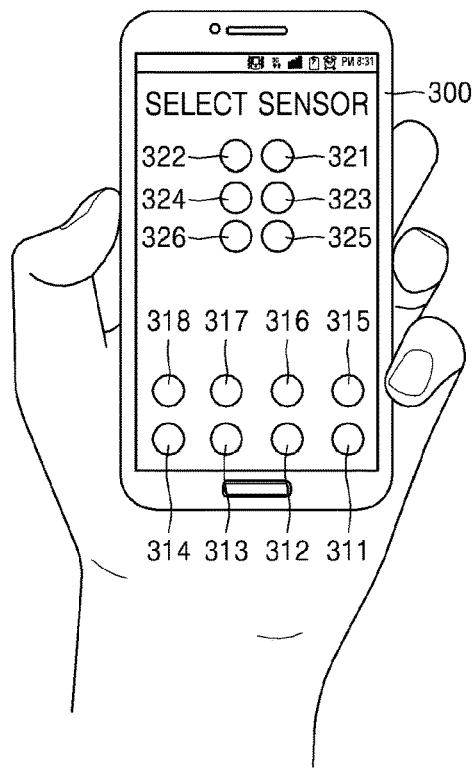
FIGS. 16A through 16F illustrate screens on which a manual selection mode of the apparatus for analyzing living body information of FIG. 12 is performed according to the flowchart of FIG. 15.

Referring to FIG. 16A, in the automatic selection mode, a sensor selection screen may be provided on a display unit of the apparatus 300. The sensor selection screen may display an arrangement of sensors positioned on a rear surface of the apparatus 300. The user may select two sensors by considering the hand that is holding the apparatus 300 and the arrangement of the sensors.

Figure 16B:
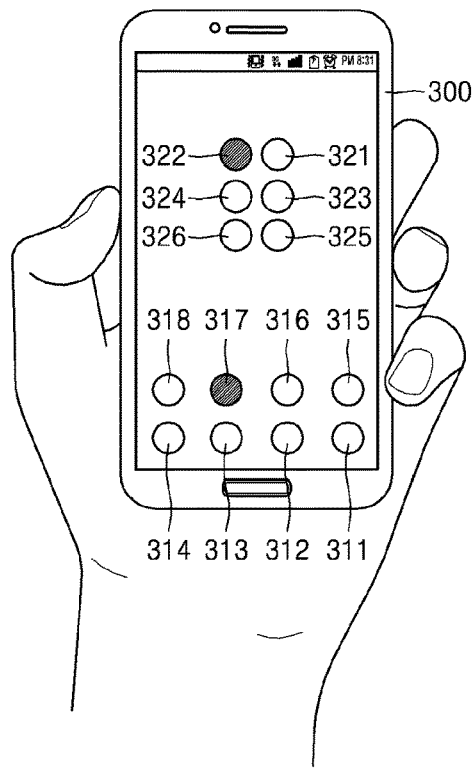

Referring to FIG. 16B, the 1-7 pulse wave sensor 317 and the 2-2 pulse wave sensor 322 are selected. The 1-7 pulse wave sensor 317 and the 2-2 pulse wave sensor 322 are located at positions that satisfy a requirement for a difference in distances from the heart of the user in consideration of the form of the hand holding the apparatus 300 for analyzing living body information. In addition, pulse wave signals may be detected and SNRs of the pulse wave signals may be measured from the 1-7 pulse wave sensor 317 and the 2-2 pulse wave sensor 322 to determine whether the 1-7 pulse wave sensor 317 and the 2-2 pulse wave sensor 322 are appropriate. The apparatus 300 detects pulse wave signals from the 1-7 pulse wave sensor 317 and the 2-2 pulse wave sensor 322 so as to analyze living body information.

Figure 16C:
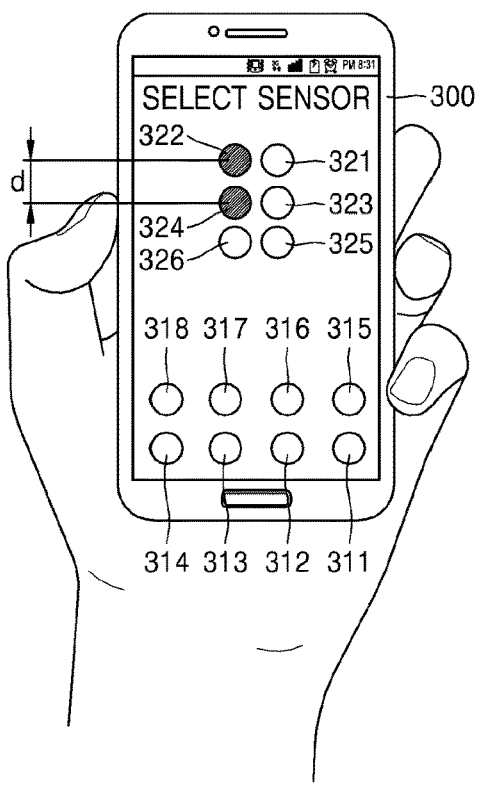

Referring to FIG. 16C, the 2-2 pulse wave sensor 322 and the 2-4 pulse wave sensor 324 are selected. The 2-2 pulse wave sensor 322 and the 2-4 pulse wave sensor 324 are located at positions that satisfy, in consideration of the form of the hand holding the apparatus 300 for analyzing living body information, a requirement regarding a distance with respect to the heart of the user when a distance d between two sensors satisfies a predetermined condition, for example, when the distance d is equal to or greater than 1 cm. In addition, pulse wave signals may be detected and SNRs of the pulse wave signals may be measured from the 2-2 pulse wave sensor 322 and the 2-4 pulse wave sensor 324 to determine whether the 2-2 pulse wave sensor 322 and the 2-4 pulse wave sensor 324 are appropriate. The apparatus 300 for analyzing living body information detects pulse wave signals from the 2-2 pulse wave sensor 322 and the 2-4 pulse wave sensor 324 so as to analyze living body information.

Figure 16D:
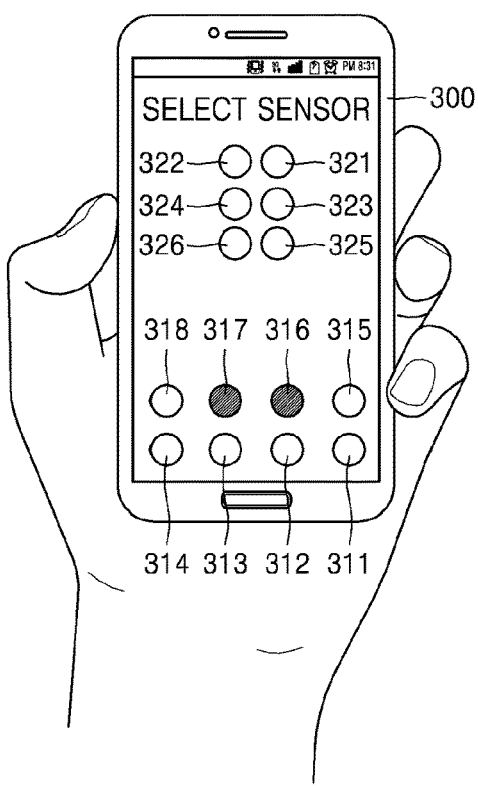
Figure 16E:
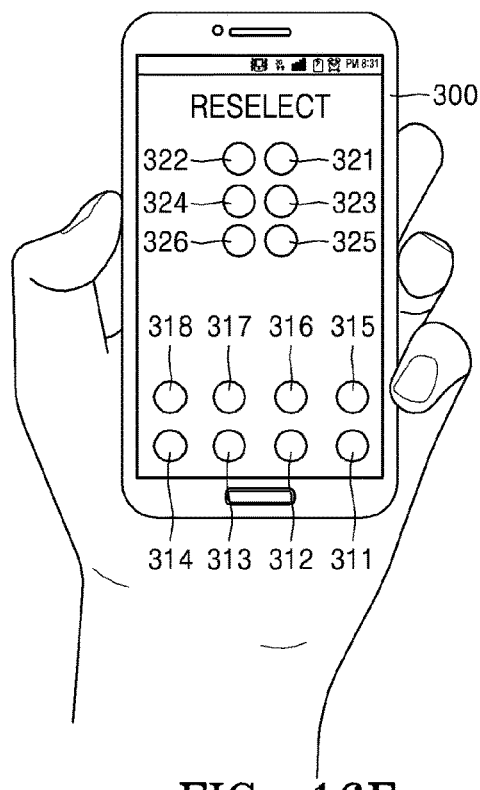
Figure 16F:
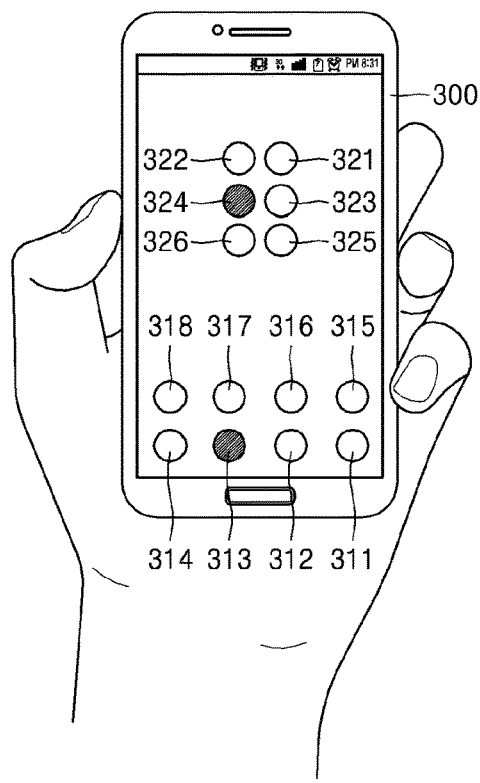

Referring to FIG. 16D, the 1-6 pulse wave sensor 316 and the 1-7 pulse wave sensor 317 are selected. The 1-6 pulse wave sensor 316 and the 1-7 pulse wave sensor 317 are located at two points on the palm, which are determined to be at the same distance from the heart of the user or at a distance less than a predetermined distance from the heart, and thus may be determined as not satisfying a selection requirement. In this case, as shown in FIG. 16E, a screen for requesting reselection may be provided on the display unit of the apparatus 300 for analyzing living body information in operation S53. As illustrated in FIG. 16F, when the 1-3 pulse wave sensor 313 and the 2-4 pulse wave sensor 324 are selected, and it is determined that a selection condition is met, the apparatus 300 for analyzing living body information detects pulse wave signals from the 1-3 pulse wave sensor 313 and the 2-4 pulse wave sensor 324 in operation S54.

As described above, pulse wave signals detected from two pulse wave sensors that are selected in the automatic mode or the manual mode may be analyzed in operation S33 and living body information is analyzed based on the analyzed pulse wave signals in operation S34.

The analyzed living body information may be compared with a reference value to thereby determine a health state of the user in operation S35. An analysis result may be displayed on the display unit and stored in the memory in operation S36.

Figure 17:
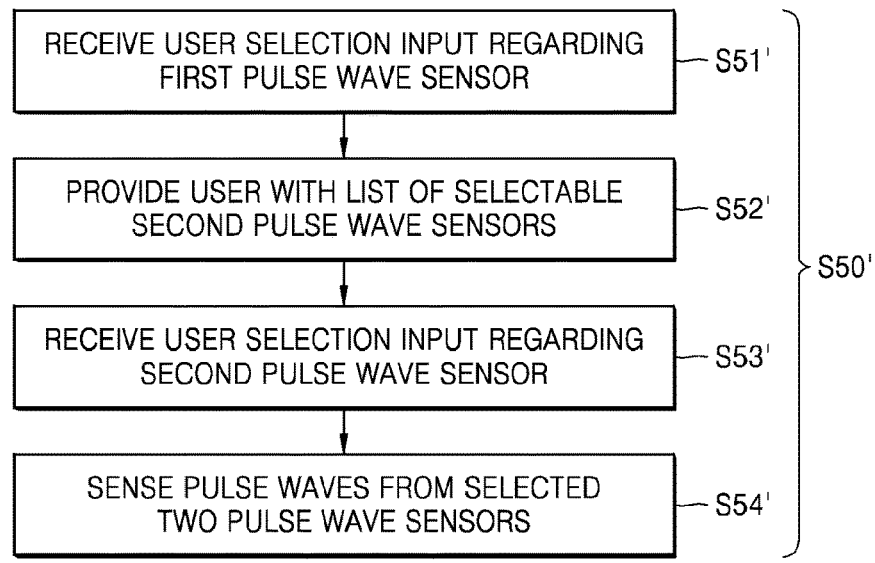
FIG. 17 is a flowchart of a method of analyzing living body information, according to another exemplary embodiment, in which a manual selection mode is performed, wherein the method of FIG. 17 is a modified example of the method of FIG. 15.

FIG. 17 is a flowchart of a method of analyzing living body information according to another exemplary embodiment, in which a manual selection mode S50' is performed, wherein the method of FIG. 17 is a modified example of the method of FIG. 15. FIGS. 18A through 18E illustrate screens on which a manual selection mode S50' of the apparatus 300 for analyzing living body information of FIG. 12 is performed according to the flowchart of FIG. 17.

Referring to FIG. 17, the apparatus 300 first receives a user selection input regarding a first pulse wave sensor from a user.

Figure 18A:
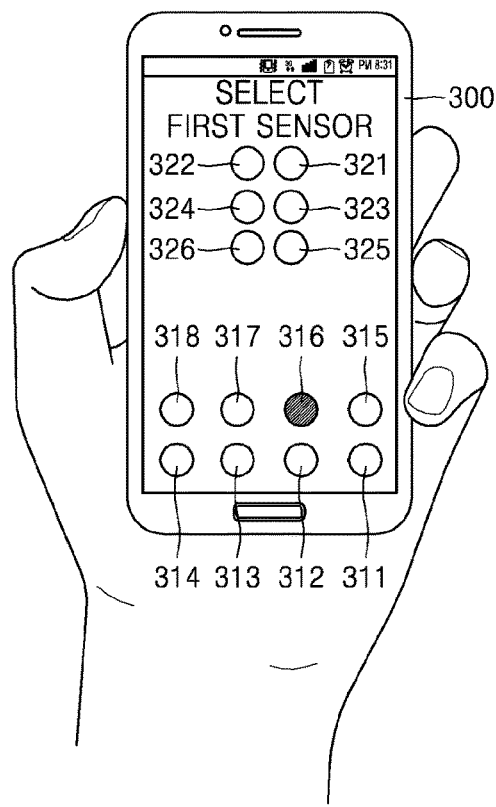
FIGS. 18A through 18E illustrate screens on which a manual selection mode of the apparatus for analyzing living body information of FIG. 12 is performed according to the flowchart of FIG. 17.

As illustrated in FIG. 18A, a first sensor selection screen may be provided on the apparatus 300 for analyzing living body information. The first sensor selection screen shows that the 1-6 pulse wave sensor 316 is selected by the user.

Figure 18B:
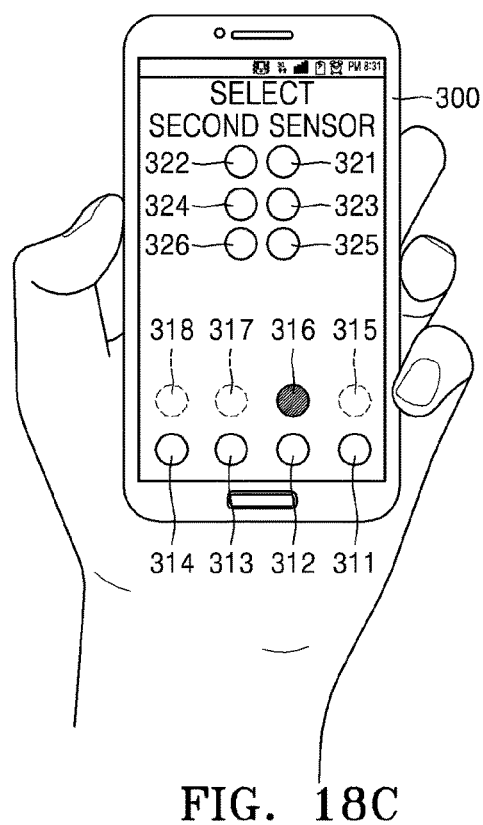

Next, the apparatus 300 for analyzing living body information provides the user with a list of selectable second pulse wave sensors in operation S52'. As shown in FIG. 18B, a screen on which selectable sensors are activated and not selectable sensors are inactivated is provided as a second sensor selection screen. The 2-1 through 2-6 pulse wave sensors 321 through 326 are activated, and the 1-1 through 1-4 pulse wave sensors 311 through 314 are activated. The 1-5 pulse wave sensor 315, the 1-7 pulse wave sensor 317, and the 1-8 pulse wave sensor 318 which are determined to be the at the same distance from the heart of the user as the 1-6 pulse wave sensor 316 that is selected or determined to be at a distance less than a predetermined distance from the heart of the user are inactivated.

Figure 18C:
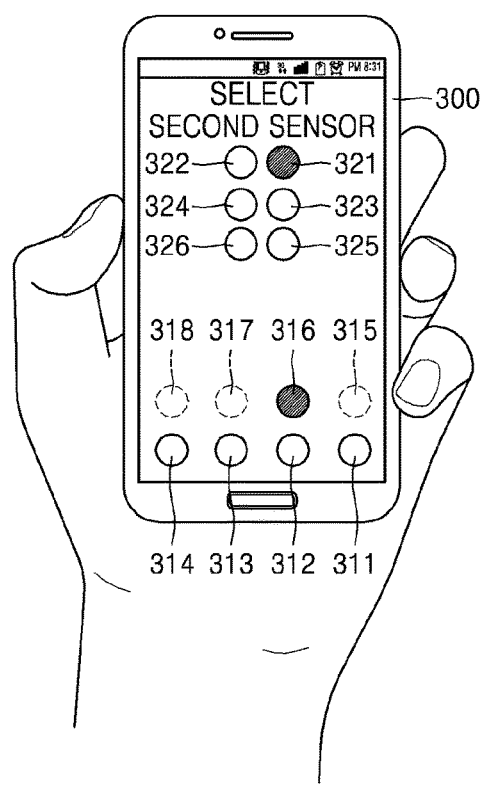

Next, the apparatus 300 receives a user selection input regarding a second pulse wave sensor in operation S53'. Referring to FIG. 18C, the 2-1 pulse wave sensor 324 is selected.

In the operation S54', the apparatus 300 detects pulse wave signals from the 1-6 pulse wave sensor 316 and the 2-1 pulse wave sensor 324 that are selected.

Figure 18D:
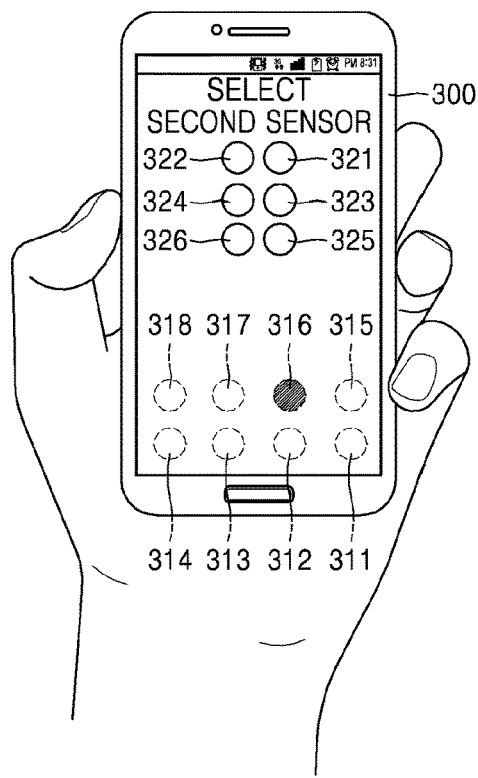
Figure 18E:
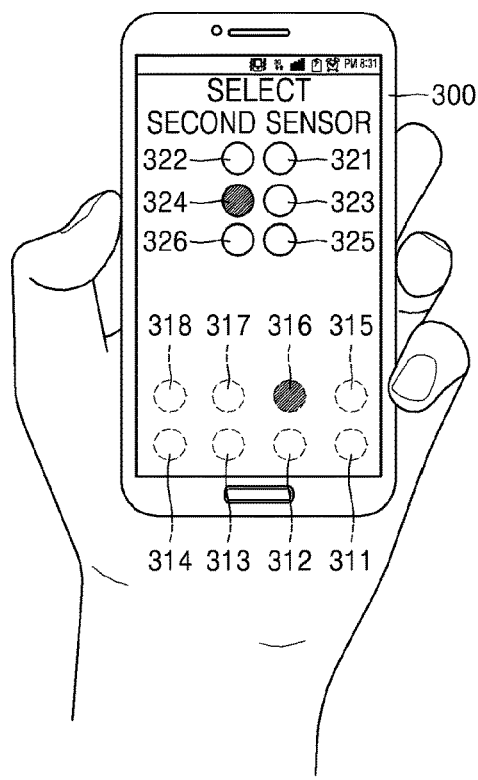

Meanwhile, a screen providing a list of selectable second pulse wave sensors may be modified to a screen as shown in FIG. 18D. In the screen of FIG. 18D, only a first pulse wave sensor group in an upper portion of the apparatus 300 for analyzing living body information is activated to be selectable. In order that a sufficient distance is provided between two selected pulse wave sensors, only the rest of the pulse wave sensors, excluding the group of the selected 1-6 pulse wave sensor 316 that has been selected as the first pulse wave sensor, are activated to be selectable. Next, as illustrated in FIG. 18E, the 2-4 pulse wave sensor 324 is selected by the user, and the apparatus 300 detects pulse wave signals from the 1-6 pulse wave sensor 316 and the 2-4 pulse wave sensor 324 and analyzes living body information.

According to the apparatus and method for analyzing living body information, living body information may be acquired using living body signals respectively detected at a plurality of points of an object. Also, measurement accuracy may be increased by arranging two pulse wave sensors so that sufficient distances are provided between the plurality of points, without using a complicated circuit element or without increasing a calculation amount.

The apparatus for analyzing living body information may be implemented in the form of a portable communication device, and when the user uses the apparatus in daily life, pulse wave sensors that spontaneously touch the body of the user increase convenience in terms of measurement and analysis.

The device described herein may comprise a processor, a memory for storing program data and executing it, a permanent storage such as a disk drive, a communications port for handling communications with external devices, and user interface devices, including a touch panel, keys, etc. When software modules or algorithms are involved, these software modules may be stored as program instructions or computer readable codes executable on the processor on a computer-readable media. Examples of the computer-readable media include magnetic storage media (e.g., read-only memory (ROM), random-access memory (RAM), floppy disks, or hard disks), optical reading media (e.g., CD-ROMs or Digital Versatile Disc (DVDs)). The computer readable recording medium can also be distributed over network coupled computer systems so that the computer readable code is stored and executed in a distributed fashion. This media can be read by the computer, stored in the memory, and executed by the processor.

The exemplary embodiments may be described in terms of functional block components and various processing steps. Such functional blocks may be realized by any number of hardware and/or software components configured to perform the specified functions. For example, the exemplary embodiments may employ various integrated circuit components, e.g., memory elements, processing elements, logic elements, look-up tables, and the like, which may carry out a variety of functions under the control of one or more microprocessors or other control devices. Similarly, where the elements of the exemplary embodiments are implemented using software programming or software elements the inventive concept may be implemented with any programming or scripting language such as C, C++, Java, assembler, or the like, with the various algorithms being implemented with any combination of data structures, objects, processes, routines or other programming elements. Functional aspects may be implemented in algorithms that execute on one or more processors. Furthermore, the exemplary embodiments could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a" and "an" and "the" and similar referents in the context of describing the exemplary embodiments (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein can be performed in any suitable order unless otherwise indicated herein or otherwise clearly contradicted by context. The use of any and all examples, or exemplary language (e.g., "such as") provided herein, is intended merely to better illuminate the inventive concept and does not pose a limitation on the scope of the exemplary embodiments unless otherwise claimed.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for analyzing living body information, the apparatus comprising:
   a plurality of pulse wave sensors configured to detect a pulse wave signal of a user and disposed on a rear surface of the apparatus;
   a processor configured to analyze the living body information of the user based on the detected pulse wave signal; and
   a display configured to display the analyzed living body information and disposed on a front surface of the apparatus,
   wherein the apparatus is configured to be held with one hand of the user,
   the plurality of pulse wave sensors comprises at least a first pulse wave sensor and a second pulse wave sensor, and
   the first pulse wave sensor is disposed apart from the second pulse wave sensor in a diagonal direction, on the rear surface of the apparatus, so that the first pulse wave sensor and the second pulse wave sensor are simultaneously touchable by a finger and a palm of the one hand of the user, respectively.

2. The apparatus of claim 1, wherein:
   the first pulse wave sensor is configured to detect a first pulse wave signal from the finger of the user when the user holds the apparatus with the hand; and
   the second pulse wave sensor is configured to detect a second pulse wave signal from the palm of the hand when the user holds the apparatus with the hand.

3. The apparatus of claim 1, wherein the processor comprises:
   a selection unit configured to select the first pulse wave sensor and the second pulse wave sensor among the plurality of pulse wave sensors to obtain a first pulse wave signal and a second pulse wave signal respectively from the first pulse wave sensor and the second pulse wave sensor; and
   an analyzing unit configured to analyze the living body information based on the first pulse wave signal and the second pulse wave signal.

4. The apparatus of claim 2, wherein:
   a difference between a first distance, which is measured from the first pulse wave sensor to a heart of the user, and a second distance, which is measured from the second pulse wave sensor to the heart, is equal to or greater than 1 cm when the user holds the apparatus with the hand.

5. The apparatus of claim 3, wherein:
   the selection unit is further configured to select the first pulse wave sensor positioned to detect the first pulse wave signal from the finger of the user and the second pulse wave sensor positioned to detect the second pulse wave signal from the palm of the hand when the user holds the apparatus with the hand.

6. The apparatus of claim 3, wherein the selection unit is further configured to select the first pulse wave sensor and the second pulse wave sensor by comparing signal levels of pulse waves respectively sensed from each of the plurality of pulse wave sensors.

7. The apparatus of claim 3, wherein the selection unit is further configured to receive a user input that instructs the apparatus to select the first and the second pulse wave sensors, and activate the first pulse wave sensor and the second pulse wave sensor to detect the first pulse wave signal and the second pulse wave signal.

8. The apparatus of claim 3, wherein the analyzing unit is further configured to extract predetermined characteristic points from the first pulse wave signal and the second pulse wave signal.

9. The apparatus of claim 8, wherein the first and second pulse wave signals are indicated as a function of a voltage variation with respect to time, and the characteristic points include a peak value of the function.

10. The apparatus of claim 6, wherein the analyzing unit is further configured to calculate a pulse transit time (PTT) from a time difference between a characteristic point of the first pulse wave signal and a corresponding characteristic point of the second pulse wave signal.

11. The apparatus of claim 10, wherein the analyzing unit is further configured to analyze vascular compliance, a blood flow rate, blood viscosity, an arteriosclerosis degree, systolic blood pressure, or diastolic blood pressure based on a distance between the selected two pulse wave sensors and the PTT.

12. The apparatus of claim 1, further comprising a memory configured to store reference values with respect to the living body information of the user.

13. The apparatus of claim 12, wherein the processor comprises a diagnosis unit configured to compare a result of analyzing the living body information with the reference values, and determine an abnormality of a health state of the user.

14. The apparatus of claim 1, further comprising a wireless communication unit.

15. The apparatus of claim 1, wherein the apparatus is a smartphone.

16. A method of analyzing living body information by a mobile device, the mobile device including a display disposed on a front surface of the mobile device, and a first pulse wave sensor and a second pulse wave sensor disposed on a rear surface of the mobile device, the rear surface opposing the front surface, the method comprising:

detecting a first pulse wave signal and a second pulse wave signal respectively from a finger and a palm of a hand of a user, while the finger and the palm are in contact with the first pulse wave sensor and the second pulse wave sensor, respectively, the first pulse wave sensor being disposed apart from the second pulse wave sensor in a diagonal direction, on the rear surface of the mobile device; and analyzing living body information based on the first pulse wave signal and the second pulse wave signal.

17. The method of claim 16, wherein a difference between a first distance, which is measured from the first pulse wave sensor to a heart of the user, and a second distance, which is measured from the second pulse wave sensor to the heart, is equal to or greater than 1 cm.

18. The method of claim 16, wherein:

the first pulse wave signal and the second pulse wave signal are represented as a function of a voltage variation with respect to time, and the analyzing comprises comparing a peak value of the voltage variation function with a peak value of a differentiation function of the voltage variation function to determine a pulse transit time (PTT), and analyzing the living body information based on the PTT.

19. The method of claim 16, further comprising comparing a result of the analyzing the living body information with a reference value to determine an abnormality of a health state of the user.

20. A method of analyzing biometric information by a handheld device including a plurality of first pulse wave sensors which are disposed in a first region on a rear of the handheld device and a plurality of second pulse wave sensors which are disposed in a second region on the rear of the handheld device, the method comprising:

identifying first pulse wave sensors and second pulse wave sensors which are in contact with a user, among the plurality of first pulse wave sensors and the plurality of second pulse wave sensors; and selectively activating at least one of the identified first pulse wave sensors and at least one of the identified second pulse wave sensors in response to a distance between the at least one of the identified first pulse wave sensors in the first region and the at least one of the identified second pulse wave sensors in the second region being greater than a predetermined distance.

21. The method of claim 20, further comprising:

obtaining a first pulse wave signal and a second pulse wave signal from the activated at least one first pulse wave sensor and the activated at least one second pulse wave sensor, respectively, and determining a blood pressure level based on the first pulse wave signal and the second pulse wave signal.

* * * * *